United States Patent
Winkenbach et al.

(10) Patent No.: US 6,423,015 B1
(45) Date of Patent: Jul. 23, 2002

(54) ANTHROPOMETRIC MEASURING DEVICE

(76) Inventors: Laurent Winkenbach, Communal 9, 2400 Le Locle; Alessandro Ferraroli, Via delle Rose 16, 6963 Pregassona, both of (CH)

( * ) Notice: Subject to any disclaimer, the term of this patent is extended or adjusted under 35 U.S.C. 154(b) by 0 days.

(21) Appl. No.: 09/699,085

(22) Filed: Oct. 27, 2000

(30) Foreign Application Priority Data

Oct. 30, 1999 (CH) .............................................. 99/1983

(51) Int. Cl.[7] .................................................. A61B 5/00
(52) U.S. Cl. ...................................................... 600/587
(58) Field of Search .............................. 600/587, 592, 600/594, 595

(56) References Cited

U.S. PATENT DOCUMENTS

| | | | | |
|---|---|---|---|---|
| 4,665,928 A | * | 5/1987 | Linial et al. ................ | 600/595 |
| 4,670,781 A | * | 6/1987 | Aubert et al. ............... | 600/587 |
| 4,699,156 A | * | 10/1987 | Gracovetsky ............... | 600/595 |
| 4,786,925 A | * | 11/1988 | Landwehr ................... | 600/587 |
| 6,186,961 B1 | * | 2/2001 | Hanoun ....................... | 600/587 |
| 6,231,527 B1 | * | 5/2001 | Sol ............................. | 600/595 |

* cited by examiner

*Primary Examiner*—Max Hindenburg
(74) *Attorney, Agent, or Firm*—McGlew and Tuttle, P.C.

(57) ABSTRACT

Anthropometric measuring device for determining characteristics relating to the skeleton of an individual (12). This device includes:

- a podium (10) on which the individual (12) takes his place,
- marks (48) arranged on the body of said individual (12), at places corresponding to the position of the joints,
- photographing means (14) of the digital type for recording the visible data concerning the individual placed on the podium,
- a computer (52) provided with a program arranged so as to determine the structure of the skeleton and to calculate the dimensions of a tool which will be handled by said individual.

The assembly is arranged so that the dimensions selected allow the individual to use said tool with the minimum effort for the maximum effect.

18 Claims, 3 Drawing Sheets

ANTHROPOMETRIC MEASURING DEVICE

FIELD OF THE INVENTION

The present invention concerns anthropometric measuring devices. It concerns more particularly devices for determining characteristics relating to an individual's skeleton or frame.

In the following description, the word <<tool>> will refer to a mechanical object with which the individual interacts by means of his hands and/or his feet.

BACKGROUND OF THE INVENTION

Certain tools, such as a bicycle, for example, require significant effort by the individual who is using it. The efficiency of the effort made varies considerably according to whether or not the tool is dimensioned so that it is adapted to the morphology of the individual. During extended use of the tool, unsuitable dimensions may cause problems such as inflammation of the joints, ligaments or muscles, for example. It is thus important to be able to adapt the tool to its user in an optimum manner.

In the case of a bicycle, the FSP Ferraroli company of Lugano (Switzerland) has developed a simulator including, like a bicycle, a frame, a saddle, a handlebar and a pedal and bottom bracket bearing assembly, and on which a potential user is subjected to tests, to measure the effort which he makes by pedaling in given conditions. This simulator allows the conditions of use to be modified and more particularly the dimensions of the frame, the handlebar and the pedal and bottom bracket bearing assembly, as well as the position of the saddle.

The pedal and bottom bracket bearing assembly is connected to a drive system coupled to an electromagnetic device, which measures the work done. It further includes means for measuring physiological parameters allowing the effort made by the user in certain conditions to be determined. The ratio between the work done and the effort made determines the yield obtained. On this simulator, most of the dimensions can be modified, such as, for example, those of the frame, the position and width of the handlebar, the length of each of the pedal cranks, etc. With a simulator of this type, it is possible, by trial and error, to determine the most favorable dimensions for an individual.

Over time, those skilled in the art have demonstrated correlations between the dimensions of the individual and those of the tool which he wishes to use, structured in the form of tables or graphs. Usually, those skilled in the art measure, by means of a measuring tape, the height of the individual, the length of his legs and thighs, that of his arms and his trunk. From this and the aforementioned tables, it is possible to preset the measuring apparatus so as to minimize the trial and error.

SUMMARY OF THE INVENTION

Practice has however revealed that individuals very often have asymmetries which are difficult to detect by the usual measurements and which greatly contribute to the health problems referred to above. These asymmetries appear during tests on the simulator and result in a tool which compensates for them being made. However, this involves numerous tests requiring a lot of time, hence an increase in the cost of the tool. The device according to the invention allows this time to be considerably reduced. Moreover, when the optimum result is not sought, it is possible to make a tool which comes remarkably close to it, for a low cost. This object is achieved as a result of the fact that the device according to the invention includes:

a podium on which the individual takes his place, marks arranged on the body of the individual, at least at places corresponding to the position of the joints, digital photographing means for recording the visible data concerning the individual placed on the podium, and a computer provided with a program arranged so as to determine the structure of the skeleton and to calculate the dimensions of a tool which will be handled by the individual being examined.

all of which is arranged so that the dimensions selected allow the individual to use this tool with the minimum effort for the maximum effect.

Practical tests carried out show that the best results were obtained when the individual concerned is examined in a standing position. In this position, the dimensions defined during the measurement allow a tool to be made with a yield of close to 85% of the optimum.

During tests, it became apparent that with only one photograph, even a front view, the data able to be collected was too limited. It would, of course, be possible to rotate the individual and to take several successive photographs, at different angles. Such a solution does not provide satisfaction, since it is difficult to establish a correlation between the different photographs.

This is why, advantageously, the device according to the invention is arranged so that the individual stands up on the podium and bears marks arranged on his body including the parts which are not directly visible from the position in which the camera is situated. Moreover, the device includes at least one mirror, placed at the side of and behind the individual with reference to the camera, so that all the marks arranged on the body can be captured by means of the camera.

It is, in particular, desirable for the device to include two mirrors arranged symmetrically.

When the tool to be dimensioned is used in a sitting position, as is the case of a bicycle, for example, the resting point formed by the saddle plays an important role. It is difficult to identify this resting point, as it is hidden by the buttocks. In order to overcome this drawback and in a particularly advantageous variant, the device also includes a column provided with vertical guide means, a horizontal measuring bar, intended to be arranged at the crutch, mounted to move vertically on said column and associated with means for generating a force oriented upwards, to ensure that the horizontal bar remains permanently in contact with the individual's body.

In order to facilitate determination of this resting point, the bar is also provided with a comparable mark to those arranged on the individual's body.

In order to ensure that data is picked up sufficiently precisely and requires only minimum calculating time, the photographing means are formed by a digital type camera. The angle of the photograph is particularly well suited when the distance measured horizontally between the camera and the individual is equal to approximately 1.5 times the height of the individual.

In the case of the bicycle, the essential effort is provided by the feet pushing on the pedals. The effort can only be made properly if the feet find satisfactory support. In order to allow knowledge relative to this parameter to be acquired, at the same time as data is collected relative to the individual's body, the podium includes a transparent plate, intended to serve as support for the individual's feet, and a mirror arranged under the plate and reflecting the image of the contact of the feet on the plate towards the camera.

BRIEF DESCRIPTION OF THE DRAWING

Other advantages and features of the invention will appear from the following description, made with reference to the annexed drawing, in which.

DESCRIPTION OF THE PREFERRED EMBODIMENT

Figure 1:
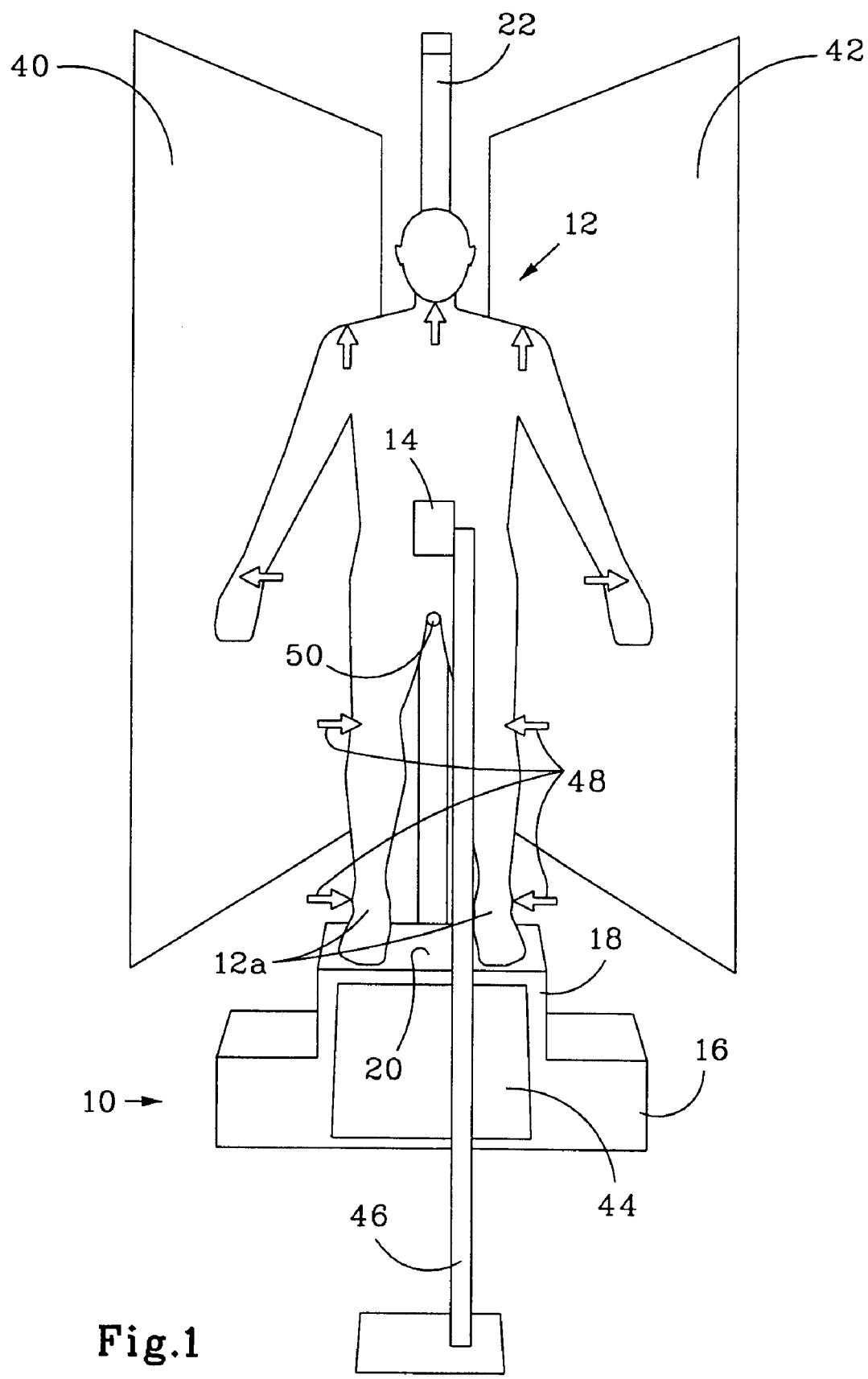
FIGS. 1 and 2 show respectively seen in a slightly offset front view and a side view, a device according to the invention, in which an individual is in position.
Figure 2:
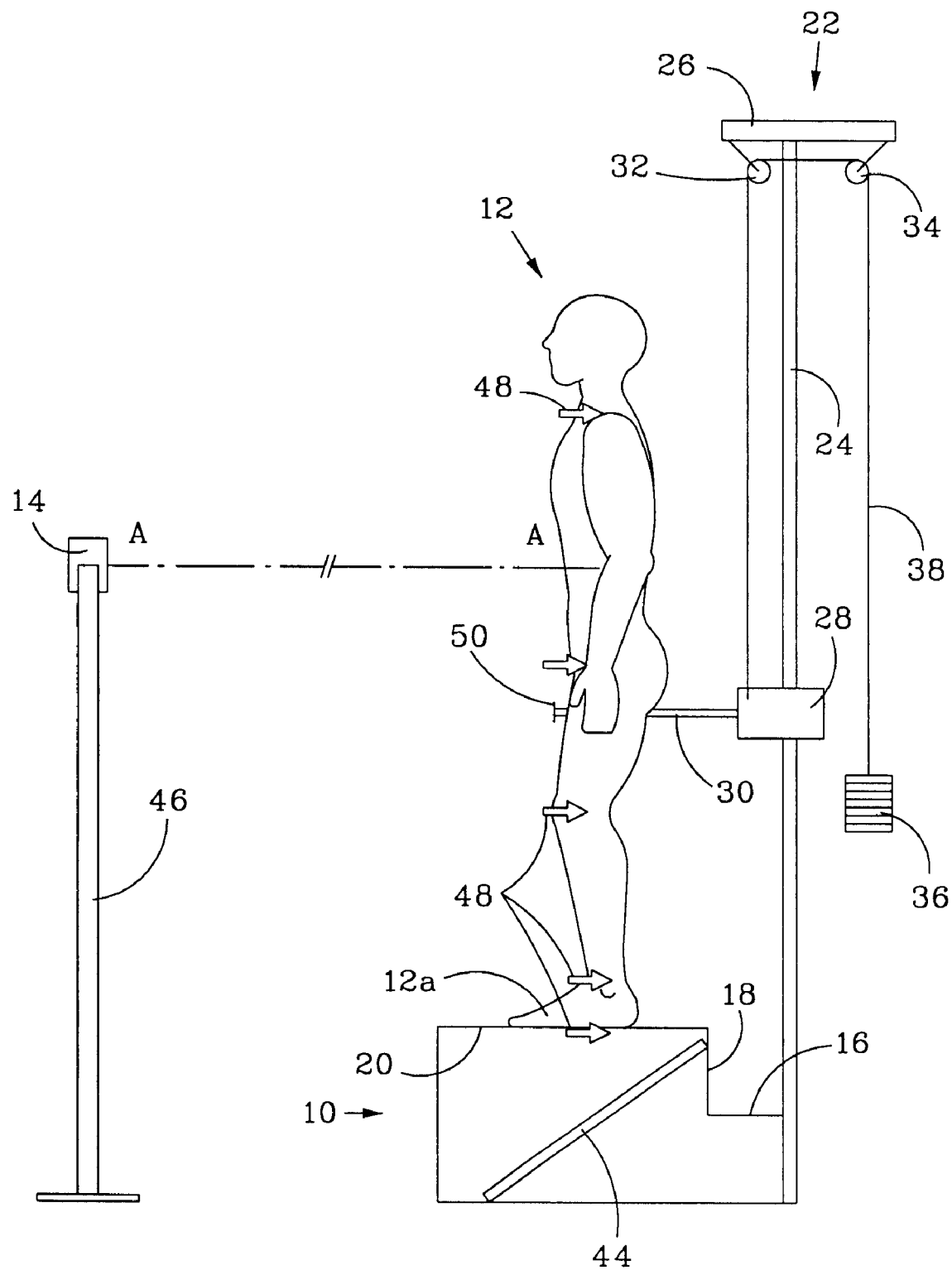

The device shown in FIGS. 1 and 2 is intended for anthropometric measurements for determining characteristics relating to the skeleton of an individual, for the purpose of manufacturing a bicycle which fits his morphology. This device includes a podium 10 intended to accommodate in succession the individuals subject to such measurements, one of them being schematically shown at 12, and a camera 14.

Podium 10 includes a base 16, of generally rectangular shape, a pedestal 18, which is arranged on base 16 and the top face of which is formed of a glass plate 20, on which individual 12 stands, his feet 12a being totally within the perimeter of plate 20.

A gibbet-shaped support 22, formed of an upright 24 and a cross-piece 26, is secured to base 16, behind pedestal 18. It serves as a support for a carriage 28 mounted so as to slide on upright 24 and provided with a horizontal bar 30 the function of which will be explained hereinafter. Cross-piece 26 carries two pulleys 32 and 34. A counterbalance weight 36 is connected to carriage 28 by a belt 38 which passes over pulleys 32 and 34. Its weight is greater than that of carriage 28, so that the latter tends to move upwards.

Base 16 further includes two mirrors 40 and 42 arranged symmetrically, on either side of gibbet-shaped support 22, at a distance of approximately 30 cm from each other, extending over a height of approximately 2 m and each being approximately 50 cm wide. The reflection surfaces of these mirrors define, between them, an angle comprised between 90° and 180°. Advantageously, mirrors 40 42 are mounted so as to pivot, about vertical axes, on supports secured to gibbet-shaped support 22, which have not been shown in the drawing in order to avoid overloading it.

Base 16 and pedestal 18 are formed of superposed hollow boxes, open towards the front. A third mirror 44 is arranged in the base, below pedestal 18. It is inclined at approximately 45° with respect to glass plate 20 and is arranged so that the bearing of the feet on the latter is framed by camera 14. A lighting system, which is not shown, is also housed in base 16, placed so as to illuminate glass plate 20.

Camera 14 is arranged on a support 46 in front of the podium, at a distance approximately equal to 1.5 times the height of individual 12 and at a height such that a horizontal axis A—A passing through the lens passes through the body of individual 12 at the level of the sternum. It is provided with a lens selected so that the image taken includes not only the individual, but also the images reflected by mirrors 40, 42 and 44.

The measuring operations include three steps:
marking the individual's body,
taking the photograph, and
calculating the features of the bicycle.

The marking operation consists in arranging marks, schematically represented by arrows 48, made for example with fluorescent ink, at the locations corresponding to the significant points of the body, both on the front, the back and the sides, directly on the body or on a skin tight garment.

From among these locations, the joints of the shoulders and wrists, hips, knees and ankles will be noted in particular.

Individual 12 then takes his place on podium 10, turned towards camera 14, his feet arranged on glass plate 20. Bar 30 is placed at the crutch, so that it projects slightly forwards. It is provided with a disc 50 having comparable features to those of marks 48. It is held in place via the effect of counterbalance weight 36.

By illuminating individual 12 with an ultraviolet light source of a conventional type, marks 48 and disc 50 appear in particularly high contrast on the body image.

The image, taken by camera 14, includes a front view of the individual, two side and back views, reflected by mirrors 40 and 42 and a contact view of the feet reflected by mirror 44. These images are defined by the points formed by the matrix of photoelectric sensors of the digital camera. Each point can thus be characterized by a coordinate, in a three dimensional referential system, the depth being defined by the images reflected by mirrors 40 and 42.

Figure 3:
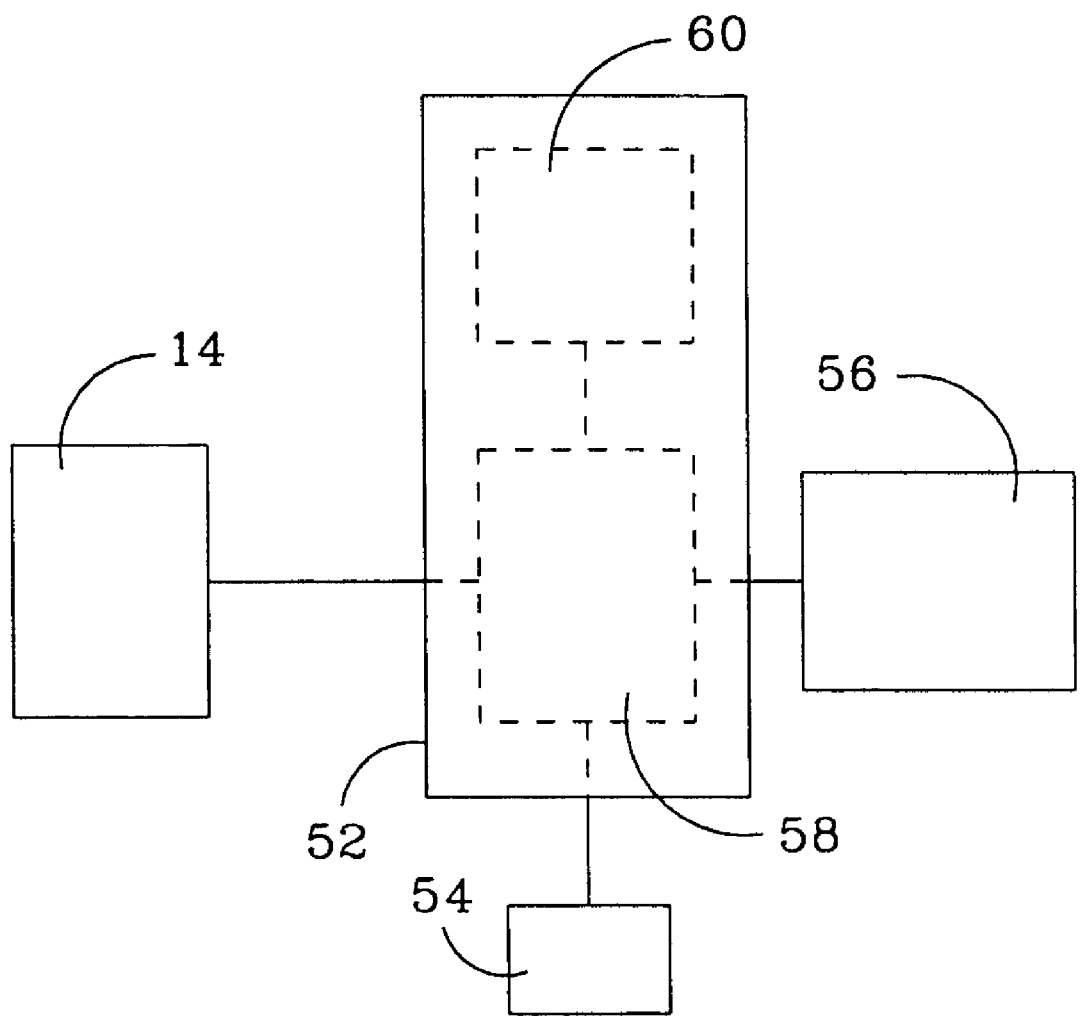
FIG. 3 shows a logic diagram of said device.

In order to process these images, the device includes calculating means shown schematically in FIG. 3, which essentially include a computer 52 provided with a control keyboard 54 and a printer 56. Computer 52 includes, in particular, a calculating unit 58 and a memory 60 which contains the control software. It is connected to camera 14, directly or via a diskette containing, in binary form, the data relating to the images taken.

First of all, computer 52 calculates, from the front view and lateral views reflected by mirrors 40 and 42, i.e. from the coordinates of the points concerned, the parameters of the skeleton of individual 12. It determines more particularly the length of the arms, the tibia and femurs, the distances between the hips and the shoulders, for both the right side and the left side. Consequently, it is possible to show up any asymmetry.

Once the skeleton parameters are known, it is then easy to introduce them into the tables defined from the results obtained by means of the apparatus marketed by the aforementioned FSP Ferraroli company, which establish correlations between the skeleton parameters and the measurements of the bicycle elements.

Thus, the dimensions of the trunk and arms define the space between the saddle and the handlebar, while the length of the legs determines the distance between the saddle and the pedals. More precisely, the legs define the height of the saddle, while the ratio of the lengths of the femur and the tibia allow the inclination of the vertical frame tube to be calculated.

The dimensions calculated can then be introduced into the simulator in order to optimize the bicycle. They can also be made legible by means of printer 56 and introduced manually.

When the requirement level is lower, corresponding substantially to 85% of the optimum, the mechanic can manufacture a bicycle which best corresponds at best to the morphology of individual 12 on the basis of the data defined by the printer alone. In a variant, this data may be directly introduced into a pre-programmed digitally controlled machine, which can directly manufacture the parts to the proper dimensions.

The image reflected by mirror 44 determines whether the individual is seated satisfactorily, or whether the arch of one and/or both feet poses a problem and requires a support.

It goes without saying that the photographs, or the parameters determined by the computer, are stored in the memory, so that it is possible to follow, over time, the evolution of a person's morphology, and, if necessary, to adapt the bicycle as a function of the recorded modifications.

In the embodiment described hereinbefore, the device allows a bicycle to be dimensioned in a particularly efficient manner and for a modest cost. Such a device may also be used in other sporting fields, for the selection of cross-country ski equipment for example, but also for adapting tools, apparatus or machines the use of which requires physical effort, for example in the field of civil engineering or construction.

What is claimed is:

1. An anthropometric measuring device for determining characteristics relating to the skeleton of an individual, including:
    a podium on which the individual takes a place,
    marks arranged on the body of said individual, at places corresponding to the position of the joints chosen among the shoulders, wrists, hips, knees and ankles,
    photographing means of the digital type for recording the visible data concerning the individual placed on the podium, and
    a computer provided with a program arranged so as to determine the structure of the skeleton and to calculate the dimensions of a tool which will be handled by said individual, all of which is arranged so that the dimensions selected allow the individual to use said tool with the minimum effort for the maximum effect.

2. A device according to claim 1, arranged so that the individual stands upright on the podium and wherein he bears marks arranged on his body including the parts which are not directly visible from the position in which the photographing means are located, and at least one mirror, placed at the side of and behind said individual with reference to the photographing means, so that all the marks arranged on his body can be captured by means of said photographing means.

3. A device according to claim 2, including two mirrors arranged symmetrically.

4. A device according to claim 2, further including a column provided with vertical guide means, a horizontal measuring bar intended to be arranged at the crutch, mounted so as to move vertically on said column and associated with means for generating a force oriented upwards, to ensure that said bar remains permanently in contact with the body of the individual.

5. A device according to claim 4, wherein said bar is also provided with a mark comparable to those arranged on said body.

6. A device according to claim 2, wherein said photographing means are formed by a camera of the digital type arranged at a measured horizontal distance equal to approximately 1.5 times the height of the individual.

7. A device according to claim 6, wherein said podium includes a transparent plate intended to serve as a support for the feet of the individual and wherein a mirror is arranged under the plate and reflects the image of the contact of the feet on the plate towards the camera.

8. A device according to claim 3, further including a column provided with vertical guide means, a horizontal measuring bar intended to be arranged at the crutch, mounted so as to move vertically on said column and associated with means for generating a force oriented upwards, to ensure that said bar remains permanently in contact with the body of the individual.

9. A device according to claim 3, wherein said photographing means are formed by a camera of the digital type arranged at a measured horizontal distance equal to approximately 1.5 times the height of the individual.

10. A device according to claim 4, wherein said photographing means are formed by a camera of the digital type arranged at a measured horizontal distance equal to approximately 1.5 times the height of the individual.

11. A device according to claim 5, wherein said photographing means are formed by a camera of the digital type arranged at a measured horizontal distance equal to approximately 1.5 times the height of the individual.

12. An anthropometric measuring device for determining skeleton features of an individual, the device comprising:
    a raised platform for supporting the individual in a standing position;
    a plurality of marks, each mark being applied relative to the body of the individual at locations of joints including at least two or more of a left shoulder, a right shoulder, a left wrist, a right wrist, a left hip, a right hip, a left knee, a right knee, a left ankle and a right ankle;
    a mirror arrangement including at least one of a left rear mirror for reflecting a left rear side of the individual and marks thereon and a right rear mirror for reflecting a right rear side of the individual and marks thereon;
    a digital camera recording visible data concerning the individual placed on the platform, the visible date including data from one or more of the left rear side of the individual and the right rear side of the individual and including recording the plurality of marks; and
    a computer provided with a program for determining the structure of the skeleton of the individual, based on the relative position of the marks and calculating dimensions of a tool which will be handled by said individual to allow the individual to use said tool with the minimum effort for the maximum effect.

13. A device according to claim 12, wherein said mirror arrangement includes two mirrors arranged symmetrically.

14. A device according to claim 12, further including a column provided with vertical guide means, a horizontal measuring bar arrangable at the crotch of the individual and mounted to move vertically on said column and associated with means for biasing the bar upwards to maintain the bar in contact with the body of the individual.

15. A device according to claim 14, wherein said bar is also provided with a mark.

16. A device according to claim 12, wherein said digital camera is arranged at a measured horizontal distance equal to approximately 1.5 times the height of the individual.

17. A device according to claim 16, wherein said platform includes a transparent plate intended to serve as a support for the feet of the individual and wherein a mirror is arranged under the plate and reflects the image of the contact of the feet on the plate towards the camera.

18. An anthropometric measuring device for determining characteristics relating to the skeleton of an individual, the device comprising:
    a podium for supporting the individual in a standing position raised from a floor surface, the podium including a transparent plate for supporting the feet of the individual;
    a plurality of marks, each mark being applied relative to the body of the individual at locations of joints including at least two or more of a left shoulder, a right shoulder, a left wrist, a right wrist, a left hip, a right hip, a left knee, a right knee, a left ankle and a right ankle;

a mirror arrangement including at least one of a left rear mirror for reflecting a left rear side of the individual and marks thereon, a right rear mirror for reflecting a right rear side of the individual and marks thereon and a lower mirror arranged under the plate for reflecting an image of the contact of the feet of the individual on the plate towards a forward direction;

a digital camera recording visible data concerning the individual placed on the podium, the visible date including data from one or more of the left rear side of the individual and the right rear side of the individual and including recording the plurality of marks; and a computer provided with a program for determining the structure of the skeleton of the individual, based on the relative position of the marks and calculating dimensions of a tool which will be handled by said individual to allow the individual to use said tool with the minimum effort for the maximum effect.

* * * * *